United States Patent
Kotanko et al.

(10) Patent No.: US 8,419,943 B2
(45) Date of Patent: *Apr. 16, 2013

(54) METHOD OF REMOVING PROTEIN-BOUND DELETERIOUS SUBSTANCES DURING EXTRACORPOREAL RENAL REPLACEMENT TREATMENT

(75) Inventors: Peter Kotanko, New York, NY (US); Nathan W. Levin, New York, NY (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/494,506

(22) Filed: Jun. 12, 2012

(65) Prior Publication Data

US 2012/0253022 A1 Oct. 4, 2012

Related U.S. Application Data

(63) Continuation of application No. 12/579,909, filed on Oct. 15, 2009, now Pat. No. 8,206,591.

(60) Provisional application No. 61/196,254, filed on Oct. 16, 2008.

(51) Int. Cl.
*B01D 59/30* (2006.01)
*B01D 59/32* (2006.01)
*B01D 61/14* (2006.01)
*B01D 61/24* (2006.01)
*A61M 1/14* (2006.01)

(52) U.S. Cl.
USPC .......... 210/638; 210/660; 604/4.01; 604/5.01

(58) Field of Classification Search .......... 210/638, 210/644–646, 649–651, 660; 604/4.01, 5.01–5.04, 604/6.09, 29
See application file for complete search history.

(56) References Cited

U.S. PATENT DOCUMENTS

| | | | |
|---|---|---|---|
| 5,744,042 A | 4/1998 | Stange et al. | |
| 7,615,158 B2 | 11/2009 | Sternby et al. | |
| 8,206,591 B2 | 6/2012 | Kotanko et al. | |
| 2009/0139930 A1 | 6/2009 | Sternby et al. | |

OTHER PUBLICATIONS

Vanholder et al. *Review on uremic toxins: Classification, concentration, and interindividual variability*, 63 Kidney International, pp. 1934-1943 (2003).

M. Mayer, *Association of Serum Bilirubin Concentration with Risk of Coronary Artery Disease*, 46 Clinical Chemistry pp. 1723-1727 (2000).

E. Beutler, T. Gelbart, and A. Demina, *Racial variability in the UDP-Glucuronosyltransferase 1 (UGT1A1) promoter: A balanced polymorphism for regulation of bilirubin metabolism?* 95 Proc. Natl. Acad. Sci., p. 8170 (1998).

S. D. Zucker, P. S. Horn, K. E. Serman, *Serum bilirubin levels in the U S. population: Gender effect and inverse correlation with colorectal cancer*, 40 Hepatology, p. 887 (2001).

R. G. Reed, *Kinetics of Bilirubin Binding to Bovine Serum Albumin and the Effects of Palmitate*, 252 J. Biol. Chem. pp. 7483-7487 (1977).

(Continued)

*Primary Examiner* — John Kim
(74) *Attorney, Agent, or Firm* — Hamilton, Brook, Smith & Reynolds, P.C.

(57) ABSTRACT

The invention is directed to a method of removing a deleterious substance bound to a protein in blood of a patient by introducing a displacer substance into the blood under conditions in which the displacer substance replaces deleterious substance bound to the protein, thereby resulting in additional unbound deleterious substance in the blood, and removing unbound deleterious substance from the blood by extracorporeal renal replacement treatment.

8 Claims, 2 Drawing Sheets

OTHER PUBLICATIONS

R. Brodersen, *Bilirubin Solubility and Interaction with Albumin and Phospholipid*, 254 J. Biol. Chem. pp. 2364-2369 (1979).

U. Kragh-Hansen, V. T. G. Chaung, and M. Otagiri, *Practical Aspects of the Ligand-Binding and Enzymatic Properties of Human Serum Albumin*, 25 Biol. Pharm. Bull. pp. 695-704 (2002).

Y. Tsutsumi, T. Maruyama, A. Takadate, H. Shimada, and M. Otagiri, *Decreased Bilirubin-Binding Capacity in Uremic Serum Caused by an Accumulation of Furan Dicarboxylic Acid*, 85 Nephron pp. 60-64 (2000).

Transmittal of International Preliminary Report on Patentability and Written Opinion, International Application No. PCT/US2009/060870 date of mailing Apr. 28, 2011.

METHOD OF REMOVING PROTEIN-BOUND DELETERIOUS SUBSTANCES DURING EXTRACORPOREAL RENAL REPLACEMENT TREATMENT

RELATED APPLICATION

This application is a continuation of U.S. application Ser. No. 12/579,909, filed on Oct. 15, 2009 now U.S. Pat. No. 8,206,591, which claims the benefit of U.S. Provisional Application No. 61/196,254, filed on Oct. 16, 2008.

The entire teachings of the above applications are incorporated herein by reference.

BACKGROUND OF THE INVENTION

For patients with acute or chronic kidney disease, some uremic toxins can be removed by extracorporeal renal replacement treatments, for example, hemodialysis. In contrast to unbound uremic toxins, protein-bound uremic toxins are difficult to remove by dialysis, because only the free (unbound) fraction of uremic toxins generally passes through the membrane of a dialyzer.

Consequently, there is a need for a new method of removing protein-bound uremic toxins during hemodialysis and other renal replacement treatments.

SUMMARY OF THE INVENTION

The present invention is directed to a method of removing a deleterious substance bound to a protein in blood of a patient comprising a) introducing a displacer substance into the blood under conditions in which the displacer substance replaces deleterious substance bound to the protein, thereby resulting in additional unbound deleterious substance in the blood, and b) removing unbound deleterious substance from the blood by extracorporeal renal replacement treatment.

In one embodiment, the deleterious substance comprises a uremic toxin. In another embodiment, the extracorporeal renal replacement treatment includes dialysis, adsorption, and filtration. In some embodiments, the protein comprises albumin. In a preferred embodiment, the displacer substance has a higher binding affinity to the protein than the deleterious substance. In another embodiment, the dialysis is hemodialysis. In yet another embodiment, the dialysis is peritoneal dialysis. In some embodiments, displacer substance is returned to the patient and provides the patient with a benefit. In a specific embodiment, the displacer substance comprises bilirubin. In certain embodiments, the uremic toxin is selected from the group consisting of p-cresol, p-cresyl sulfate, indoxyl sulfate, CMPF, and combinations thereof.

The present invention is also directed to a method of removing a deleterious substance bound to a protein in a biological liquid comprising introducing a displacer substance into the biological liquid under conditions in which the displacer substance replaces deleterious substance bound to the protein, thereby resulting in additional unbound deleterious substance in the biological liquid, and removing unbound deleterious substance from the biological liquid.

The use of competitive displacement of protein-bound uremic toxin increases the amount of previously bound uremic toxin that can be removed by hemodialysis and other renal replacement treatments.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
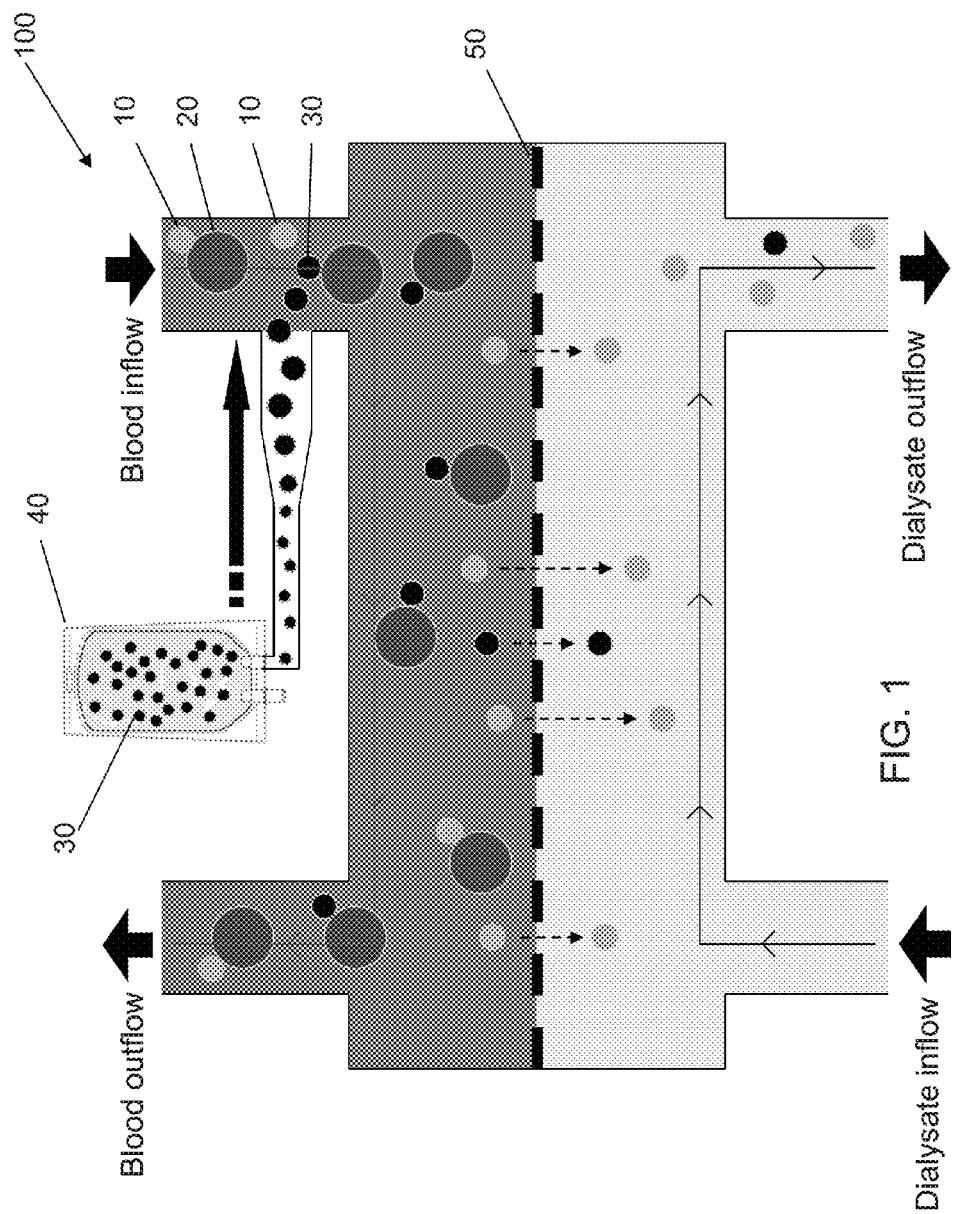
FIG. 1 is a schematic illustration of the method of the invention in a hemodialysis machine.

A description of example embodiments of the invention follows.

The present invention is directed to a method of removing a deleterious substance bound to a protein in blood of a patient comprising a) introducing a displacer substance into the blood under conditions in which the displacer substance replaces deleterious substance bound to the protein, thereby resulting in additional unbound deleterious substance in the blood, and b) removing unbound deleterious substance from the blood by extracorporeal renal replacement treatment.

Extracorporeal renal replacement treatments replace or supplement the normal function of the kidneys of a patient. Examples of extracorporeal renal replacement treatments include dialysis, for example, hemodialysis and peritoneal dialysis, and also adsorption with sorbents, such as, for example, charcoal or molecular adsorbents (molecular adsorbents recycling system (MARS)), and filtration. Hemodialysis is a particularly preferred extracorporeal renal replacement treatment.

Deleterious substances are substances that have a negative effect on physiological functions when present in the human body above threshold concentration levels. Deleterious substances include drugs and uremic toxins. Uremic toxins are substances that normally would be excreted into the urine or metabolized by the kidneys. Drugs include, for example, warfarin, salicylate, indomethacine, and furosemide.

In human biological liquids, many drugs and uremic toxins are transported as complexes bound to proteins, such as, for example, albumin and $\alpha_1$-acid glycoprotein. Biological liquids include most prominently blood, and also peritoneal fluid, interstitial fluid, and third space fluid, also called transcellular fluid, which includes cerebrospinal fluid and fluids found in the gastrointestinal tract, the urinary tract, the ducts of glands, and serous cavities. In human blood, serum albumin binds reversibly to many uremic toxins including, for example, 2-methoxyresorcinol, 3-deoxyglucosone, fructoselysine, glyoxal, hippuric acid, p-OH-hippuric acid, homocysteine, hydroquinone, indole-3-acetic acid, indoxyl sulfate, kinurenine, kynurenic acid, melatonin, methylglyoxal, n-(carboxymethyl)lysine, p-cresol, p-cresyl sulfate, pentosidine, phenol, putrescine, quinolinic acid, spermidine, spermine, and 3-carboxy-4-methyl-5-propyl-2-furan-propanoic acid (CMPF), most prominently p-cresol, p-cresyl sulfate, and CMPF. See Vanholder et al. *Review on uremic toxins: Classification, concentration, and interindividual variability*, 63 Kidney International, pp. 1934-1943 (2003).

The normal serum concentration of p-cresol in a patient is about 0.6 mg/L, and the serum concentration of p-cresol in an uremic patient can be as high as about 20.1 mg/L. For CMPF, the normal serum concentration is about 7.7 mg/L, and the uremic serum concentration can be as high as about 61.0 mg/L. Id.

Displacer substances are substances that competitively bind to a protein, preferably albumin, and thereby displace uremic toxin, such as, for example, p-cresol or CMPF, from being bound to the protein, thus increasing the concentration of free uremic toxin that can be removed by, for example, dialysis. Displacer substances include bilirubin, 1-tryptophan, 1-tryptophyl-1-tryptophan, 1-tryptophyl-1-phenylalanine, and phenylalanine. Preferred displacer substances provide a benefit when reinfused into the patient, such as, for example, a therapeutic benefit. Preferred displacer substances include bilirubin, which can prevent cardiovascular damage, and 1-tryptophan, which can be a sleep aid.

Bilirubin is a waste product formed during heme catabolism. Recent studies have shown, however, that bilirubin is also a potent physiological antioxidant that can provide important protection against atherosclerosis, coronary artery disease, and inflammation. See M. Mayer, *Association of Serum Bilirubin Concentration with Risk of Coronary Artery Disease,* 46 Clinical Chemistry pp. 1723-1727 (2000). Studies have shown that free and albumin-bound bilirubin have the potential to serve as lipid antioxidants and oxygen radical scavengers under physiological conditions, and therefore serum bilirubin concentrations in the upper portion of the reference interval for the general population can provide protection against coronary artery disease. Id. The upper portion of the reference interval is the non-toxic level for adults of serum bilirubin concentration, which is typically about 10 mg/dL for normal adults. Studies of adults with Gilbert's syndrome, who have naturally elevated concentrations of serum bilirubin, have also shown benefits of hyperbilirubinemia, such as retardation of atherogenesis and lowering the risk of colorectal cancer. See E. Beutler, T. Gelbart, and A. Demina, *Racial variability in the UDP-Glucuronosyltransferase 1 (UGT1A1) promoter: A balanced polymorphism for regulation of bilirubin metabolism?* 95 Proc. Natl. Acad. Sci., p. 8170 (1998); S. D. Zucker, P. S. Horn, K. E. Serman, *Serum bilirubin levels in the U.S. population: Gender effect and inverse correlation with colorectal cancer,* 40 Hepatology, p. 887 (2001). The non-toxic level of bilirubin for new born babies, however, is usually much lower because the blood-brain barrier is not fully developed until several weeks after birth.

Bilirubin can be used to displace protein-bound uremic toxins, such as, for example, p-cresol, p-cresyl sulfate, indoxyl sulfate, and CMPF, by competitive binding to a protein, such as, for example, albumin. Bilirubin binding to albumin is a first order reaction. See R. G. Reed, *Kinetics of Bilirubin Binding to Bovine Serum Albumin and the Effects of Palmitate,* 252 J. Biol. Chem. pp. 7483-7487 (1977). The first order association constant, $K_1$, for bilirubin to albumin has been reported to be $5.5 \times 10^7$ $M^{-1}$. See R. Brodersen, *Bilirubin Solubility and Interaction with Albumin and Phospholipid,* 254 J. Biol. Chem. pp. 2364-2369 (1979). Association constants for physiological molecules are generally reported at body temperature (37° C.). See Id. The first order association constant, $K_1$, for CMPF to albumin has been reported to be $1.3 \times 10^7$ $M^{-1}$. See U. Kragh-Hansen, V. T. G. Chaung, and M. Otagiri, *Practical Aspects of the Ligand-Binding and Enzymatic Properties of Human Serum Albumin,* 25 Biol. Pharm. Bull. pp. 695-704 (2002). Studies have shown that CMPF is one of the substances that contribute to the decreased binding capacity of bilirubin in uremic serum, and that CMPF is capable of competitively displacing bilirubin on the human serum albumin molecule, despite the lower binding affinity (association constant) of CMPF to albumin. See Y. Tsutsumi, T. Maruyama, A. Takadate, H. Shimada, and M. Otagiri, *Decreased Bilirubin-Binding Capacity in Uremic Serum Caused by an Accumulation of Furan Dicarboxylic Acid,* 85 Nephron pp. 60-64 (2000).

In a preferred case, the binding affinity (association constant) between a displacer substance and a protein is higher than the binding affinity between a uremic toxin and the protein. As described above, this is the case for competitive displacement of CMPF from albumin by bilirubin. In certain cases, it is also possible to use a displacer substance with a lower binding affinity to a protein than the binding affinity of a uremic toxin to the protein, by, for example, sufficiently increasing the concentration of the displacer substance.

Competitive binding by a displacer substance can result in the displacement of one or more uremic toxins from the protein. One or more uremic toxins can also be displaced by competitive binding by one or more displacer substances.

Turning now to FIG. 1, blood flowing into hemodialysis machine 100 contains uremic toxin 10 bound to protein 20. Displacer substance 30 is infused from container 40 into the blood near the inlet of the blood flow into the hemodialysis machine 100. A fraction of displacer molecule 30 competitively binds to the protein 20, preferably albumin, thus freeing uremic toxin 10, which can then be removed by diffusion across dialyzer membrane 50, which also removes a fraction of displacer molecule 30. Displacer substance 30, preferably bilirubin, can be infused into the blood upstream of dialyzer membrane 50, to increase the serum bilirubin concentration in the blood at the point of infusion to about 15-20 mg/dL. That concentration of bilirubin can result in an increase in the concentration of free uremic toxin, such as, for example, CMPF, to be dialyzed and removed by dialysis membrane 50, which also removes about 50% to about 70% of the bilirubin, that is, the dialysis membrane removes a sufficient amount of the displacer substance to insure that the blood outflow returned to the patient has a non-toxic serum bilirubin concentration, that is, below about 10 mg/dL.

EXEMPLIFICATION

Example 1

Uremic Toxin Displacement Model Calculations

In order to model the concept of using a displacer molecule to improve removal of albumin-bound toxins by dialysis, some basic equilibrium and kinetic constants must be known or estimated. Another necessary input is the plasma concentration of all components. For the current model calculations, bilirubin was used as the displacer molecule and 3-carboxy-4-methyl-5-propyl-2-furanpropanoic acid (CMPF) was the albumin-bound toxin; however, these calculations can be generalized to any displacer and any bound toxin if appropriate equilibrium constant information is provided. This model only considers these three molecules mentioned (albumin, bilirubin, and CMPF). Of course, there are expected to be a number of other species that bind to albumin in the plasma.

In general a binding reaction can be written as:

$$A + B \underset{k_{-1}}{\overset{k_1}{\rightleftharpoons}} AB \tag{1}$$

where A and B represent free or unbound species and AB is the bound complex. The rate of the forward or binding reaction is noted by $k_1$ and the rate of the reverse or unbinding reaction is noted by $k_{-1}$.

The equilibrium association constant can be related to the forward and reverse reaction rates as well as the species concentrations at equilibrium:

$$K_a = \frac{k_1}{k_{-1}} = \frac{[AB]}{[A]*[B]} \quad (2)$$

In order to determine the equilibrium concentrations of A, B, and AB from starting concentrations and an equilibrium association constant, a table can be made:

TABLE 1

Example ICE concentration table

|  | A | + | B | ⇔ | AB |
|---|---|---|---|---|---|
| Initial Conc. | $[A]_i$ |  | $[B]_i$ |  | 0 |
| Change | −x |  | −x |  | +x |
| Equilibrium Conc. | $[A]_i - x$ |  | $[B]_i - x$ |  | +x |

The expressions for the equilibrium concentrations in the table above can be placed into Equation 2:

$$K_a = \frac{(x)}{([A]_i - x)*([B]_i - x)} \quad (3)$$

For a known $K_a$, $[A]_i$, and $[B]_i$, Equation 3 can be solved for x, which is then replaced into Table 1 to determine equilibrium concentrations of free A, free B, and bound complex AB.

First, the two component systems are modeled, meaning binding between only bilirubin and albumin or only CMPF and albumin. These calculation are only to give an idea of how much of either bilirubin or CMPF alone could bind to albumin. In current calculations, it is assumed that there is one site on albumin where both bilirubin and CMPF compete to bind. Additional sites which may bind one or both of these could be added to future calculations. To determine how much bilirubin or CMPF is bound to albumin, a plasma concentration of albumin must be set and in these calculations it is 3850 mg/dL, which represents $[A]_i$. A range of total (bound+free) bilirubin concentrations is chosen (1-150 μM), which represents $[B]_i$. $K_a$ was taken to be 5.5E7 M$^{-1}$. Equation 3 was solved for each bilirubin concentration to yield the following results:

TABLE 2

Bilirubin-albumin binding

| Total Bilirubin Conc. (μM) | Total Bilirubin Conc. (M) | Free Bilirubin Conc. (M) |
|---|---|---|
| 1 | 1.0E−06 | 3.2E−11 |
| 2 | 2.0E−06 | 6.4E−11 |
| 5 | 5.0E−06 | 1.6E−10 |

TABLE 2-continued

Bilirubin-albumin binding

| Total Bilirubin Conc. (μM) | Total Bilirubin Conc. (M) | Free Bilirubin Conc. (M) |
|---|---|---|
| 10 | 1.0E−05 | 3.2E−10 |
| 12 | 1.2E−05 | 3.9E−10 |
| 15 | 1.5E−05 | 4.9E−10 |
| 20 | 2.0E−05 | 6.6E−10 |
| 45 | 4.5E−05 | 1.5E−09 |
| 75 | 7.5E−05 | 2.7E−09 |
| 100 | 1.0E−04 | 3.8E−09 |
| 125 | 1.3E−04 | 5.1E−09 |
| 150 | 1.5E−04 | 6.4E−09 |

The same calculations can be repeated with CMPF and albumin. The total concentration of albumin is the same, 3850 mg/dL. A range of total CMPF was chosen (10-300 mg/L) and $K_a$ was 1.3E7 M$^{-1}$. Equation 3 was solved for each CMPF concentration yielding the following results:

TABLE 3

CMPF-albumin binding

| Total CMPF Conc. (mg/L) | Total CMPF Conc. (M) | Free CMPF Conc. (M) |
|---|---|---|
| 10 | 4.2E−05 | 6.0E−09 |
| 20 | 8.3E−05 | 1.3E−08 |
| 30 | 1.2E−04 | 2.1E−08 |
| 40 | 1.7E−04 | 3.1E−08 |
| 50 | 2.1E−04 | 4.4E−08 |
| 70 | 2.9E−04 | 7.9E−08 |
| 90 | 3.7E−04 | 1.4E−07 |
| 100 | 4.2E−04 | 2.0E−07 |
| 150 | 6.2E−04 | 5.0E−05 |
| 200 | 8.3E−04 | 2.6E−04 |
| 250 | 1.0E−03 | 4.7E−04 |
| 300 | 1.2E−03 | 6.7E−04 |

When there is competition between two species for one binding site, the equations become slightly more complicated and must be solved simultaneously. The 2 reactions occurring, in general, are:

$$A + B \underset{k_{-1}}{\overset{k_1}{\rightleftharpoons}} AB \quad (4)$$

$$A + C \underset{k_{-2}}{\overset{k_2}{\rightleftharpoons}} AC$$

The table to calculate equilibrium concentrations becomes:

TABLE 4

Example ICE table for 2 simultaneous competing reactions

|  | A | + B | ⇔ AB | A | + C | ⇔ | AC |
|---|---|---|---|---|---|---|---|
| Initial | $[A]_i$ | $[B]_i$ | 0 | $[A]_i$ | $[C]_i$ |  | 0 |
| Change | $-x-y$ | $-x$ | $+x$ | $-x-y$ | $-y$ |  | $+y$ |
| Equilibrium | $[A]_i-x-y$ | $[B]_i-x$ | $+x$ | $[A]_i-x-y$ | $[C]_i-y$ |  | $+y$ |

These expressions for equilibrium concentration are again placed into equation 2:

$$K_{a1} = \frac{(x)}{([A]_i - x - y) * ([B]_i - x)} \quad (5)$$

$$K_{a2} = \frac{(y)}{([A]_i - x - y) * ([C]_i - y)} \quad (6)$$

In order to determine the equilibrium concentrations in this system of two competing reactions, both equations 5 and 6 must be solved for x and y simultaneously. With a plasma albumin concentration of 3850 mg/dL and CMPF concentration of 40 mg/L, equations 5 and 6 were solved for 3 different bilirubin concentrations (1, 10, and 20 mg/dL). The results are summarized in Table 5.

TABLE 5

Multicomponent equilibrium results

| Bilirubin Conc. (mg/dL) | Bilirubin Conc. (M) | Free Bilirubin Conc. (µM) | Free CMPF Conc. (µM) | Free Albumin (µM) | Bound/Free CMPF (unitless) |
|---|---|---|---|---|---|
| 1 | 1.7E−05 | 7.90E−04 | 3.27E−02 | 391.2 | 5085.6 |
| 10 | 1.7E−04 | 1.30E−02 | 5.37E−02 | 238.2 | 3097.1 |
| 20 | 3.4E−04 | 9.35E−02 | 1.92E−01 | 66.5 | 863.9 |

These multicomponent equilibrium results show that as the total concentration of bilirubin is increased, the amount of unbound or free toxin (CMPF) also increases. Because there are a number of other species that bind with albumin, especially in the binding site for which bilirubin and CMPF compete, one might expect that all of the albumin sites may not be available for toxin or displacer binding. In order to estimate this effect, a factor was added to the calculations to decrease the concentration of albumin that is available to participate in these reactions. This factor was varied from 25% to 75% and equations 5 and 6 were again solved for 3 bilirubin concentrations. Table 5 represents results with this factor set at 100%.

TABLE 6

Multicomponent equilibrium results - 75% albumin sites

| Bilirubin Conc. (mg/dL) | Bilirubin Conc. (M) | Free Bilirubin Conc. (µM) | Free CMPF Conc. (µM) | Free Albumin (µM) | Bound/Free CMPF (unitless) |
|---|---|---|---|---|---|
| 1 | 1.7E−05 | 1.25E−03 | 5.17E−02 | 391.2 | 3218.3 |
| 10 | 1.7E−04 | 3.26E−02 | 1.35E+01 | 238.3 | 1230.8 |
| 20 | 3.4E−04 | 2.98E+01 | 4.79E+01 | 143.8 | 2.5 |

TABLE 7

Multicomponent equilibrium results - 50% albumin sites

| Bilirubin Conc. (mg/dL) | Bilirubin Conc. (M) | Free Bilirubin Conc. (µM) | Free CMPF Conc. (µM) | Free Albumin (µM) | Bound/Free CMPF (unitless) |
|---|---|---|---|---|---|
| 1 | 1.7E−05 | 2.97E−03 | 1.23E−01 | 391.3 | 1351.8 |
| 10 | 1.7E−04 | 1.12E+01 | 3.82E+01 | 287.6 | 3.4 |
| 20 | 3.4E−04 | 1.10E+02 | 1.11E+02 | 287.4 | 0.5 |

TABLE 8

Multicomponent equilibrium results - 25% albumin sites

| Bilirubin Conc. (mg/dL) | Bilirubin Conc. (M) | Free Bilirubin Conc. (µM) | Free CMPF Conc. (µM) | Free Albumin (µM) | Bound/Free CMPF (unitless) |
|---|---|---|---|---|---|
| 1 | 1.7E−05 | 1.14E+00 | 3.89E+01 | 431.2 | 3.3 |
| 10 | 1.7E−04 | 6.91E+01 | 1.24E+02 | 431.0 | 0.3 |
| 20 | 3.4E−04 | 2.18E+02 | 1.47E+02 | 431.0 | 0.1 |

From tables 5-8 it can be seen that the amount of available albumin also has a large effect on how much CMPF is unbound or free. These results suggest that even for the smallest (25%) fraction of available albumin sites, if the local concentration of bilirubin is increased in plasma containing CMPF bound to albumin then the CMPF will become displaced and able to be removed via dialysis.

Another issue in using this displacement concept to improve removal of albumin bound toxins that must be considered is the kinetics of the binding or unbinding reaction. The time required for binding/unbinding to occur will dictate how far in advance of the dialyzer the displacer molecule must be mixed with the blood. The reaction rate for equation 1 can be written as:

$$r_A = k_1 C_A C_B - k_{-1} C_{AB} \quad (8)$$

Equation 8 can be written in terms of conversion (or fractional amount of reaction that has taken place).

$$C_{A0}\frac{dx_A}{dt} = k_1(C_A - C_{A0}x_A)(C_B - C_{A0}x_A) - k_{-1}(C_{AB} - C_{A0}x_A) \quad (9)$$

Figure 2:
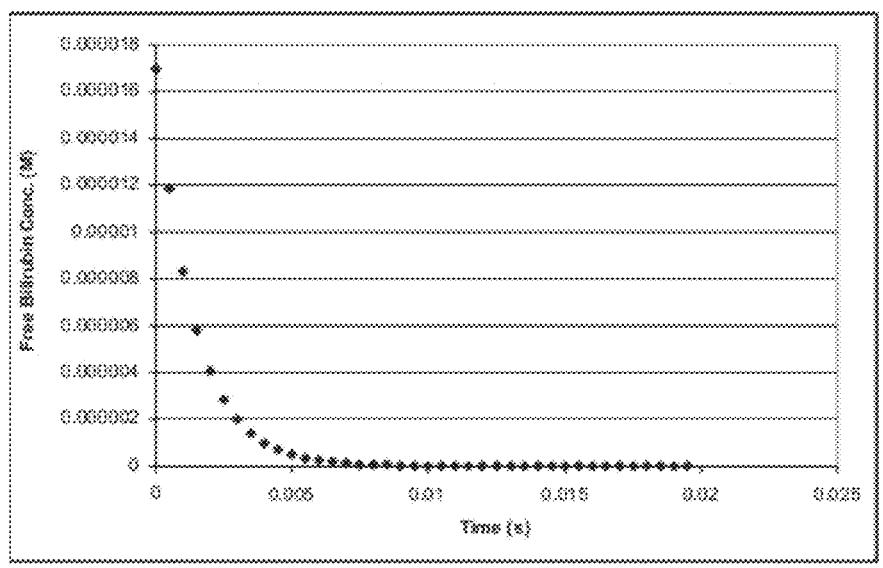
FIG. 2 is a graph of model results of binding kinetics of bilirubin and albumin.

Differential equation 9 can be solved for $x_A$ as a function of time, which will allow for the calculation of concentration as a function of time. Equations 8 and 9 can be generalized to the binding between any two species and can be solved for any species binding if reaction rate constants and starting concentrations are known. A starting albumin concentration of 3850 mg/dL and a concentration of 1 mg/dL bilirubin was used. The forward reaction rate constant was set at 1.26E6 $M^{-1}s^{-1}$ and the reverse reaction rate constant was 2.29E-2 $s^{-1}$. The results in FIG. 2 show that the binding of bilirubin to albumin reaches equilibrium in less than 0.01 seconds. This suggests that bilirubin could be added to the blood stream relatively close to the dialyzer and all displacement would have taken place before reaching the dialyzer membrane. Equation 9 can also be solved to find the time required for binding of CMPF to albumin.

Lastly, since model calculations have suggested that increasing local bilirubin concentration would in fact displace CMPF from albumin, an estimation of how much CMPF could be removed by dialysis with displacer treatment can be made. For this calculation a dialyzer KoA for unbound CMPF was estimated using known KoAs of other species and their molecular weights. A dialyzer clearance (K) can be calculated from the dialyzer KoA, blood flow rate ($Q_B$), and dialysate flow rate ($Q_D$):

$$K = \frac{Q_B \left[ \exp\left(\frac{KoA}{Q_B}\left(1 - \frac{Q_B}{Q_D}\right)\right) - 1 \right]}{\left[ \exp\left(\frac{KoA}{Q_B}\left(1 - \frac{Q_B}{Q_D}\right)\right) - \frac{Q_B}{Q_D} \right]} \quad (10)$$

The blood concentration of a species during a dialysis treatment can be calculated from the clearance (K), the volume of distribution (V), and the pre-dialysis blood concentration ($C_0$):

$$C = C_0 \exp\left(\frac{-Kt}{V}\right) \quad (11)$$

Figure 3:
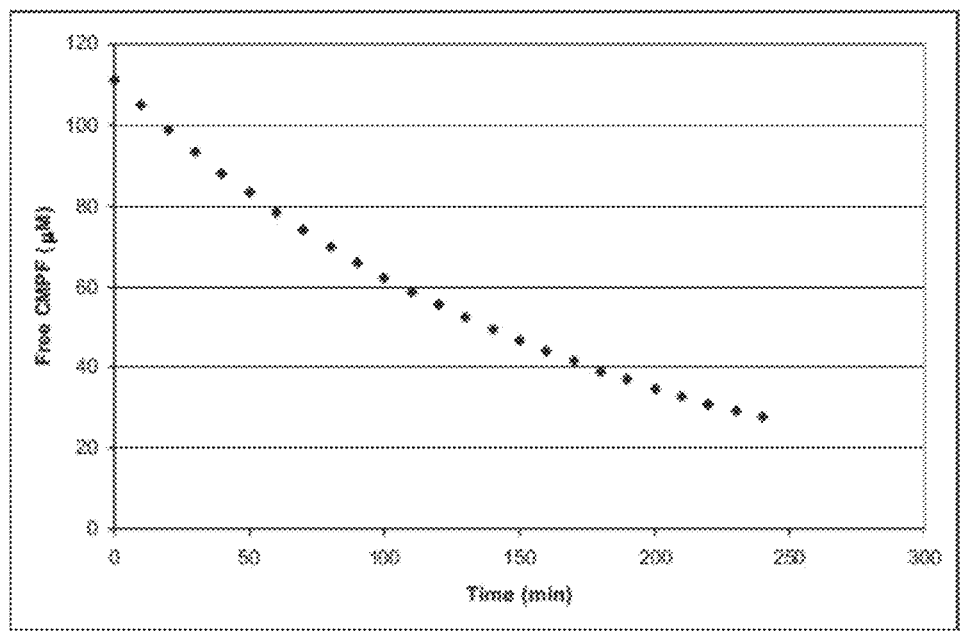
FIG. 3 is a graph of model results of the removal of CMPF by dialysis with displacer treatment.

Assuming a blood flow rate of 300 mL/min, a dialysate flow rate of 500 mL/min, a KoA of 750 mL/min, local bilirubin concentration of 20 mg/dL, 50% of albumin sites available, a 42 L distribution volume, an albumin concentration of 3850 mg/dL, and a CMPF concentration of 40 mg/L the free CMPF concentration during dialysis treatment can be calculated and is illustrated in FIG. 3. These calculations suggest that, during a 4 hour dialysis with displacer treatment, the free CMPF concentration could be reduced about 72% and around 840 mg of CMPF would be removed.

Example 2

Competitive Displacement of Indoxyl Sulfate by Bilirubin in Model Uremic Plasma

Two samples of uremic plasma (blood urea nitrogen (BUN) of about 55 mg/dL, albumin concentration of 3.82 g/dL) including indoxyl sulfate were incubated for 12 hours at 37° C. One sample also included 2 mMolar bilirubin ditauride (Bil-DT). The bilirubin containing sample showed a free indoxyl sulfate concentration of 0.93 µg/ml, while the control uremic plasma containing no Bil-DT, showed a free indoxyl sulfate concentration of 0.65 µg/ml. These results are indicative of competitive displacement of indoxyl sulfate by bilirubin.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of removing a deleterious substance bound to a protein in a biological liquid comprising:
    a) introducing a displacer substance into the biological liquid under conditions in which the displacer substance replaces deleterious substance bound to the protein, thereby resulting in additional unbound deleterious substance in the biological liquid; and
    b) removing unbound deleterious substance from the biological liquid.

2. The method of claim 1, wherein the deleterious substance comprises a drug.

3. The method of claim 2, wherein the drug comprises warfarin, salicylate, indomethacine, and furosemide.

4. The method of claim 3, wherein the protein comprises $\alpha_1$-acid glycoprotein.

5. The method of claim 4, wherein the displacer substance has a higher binding affinity to the protein than the deleterious substance.

6. The method of claim 1, wherein displacer substance is returned to the patient and provides the patient with a benefit.

7. The method of claim 6, wherein the displacer substance comprises bilirubin.

8. The method of claim 4, wherein the biological liquid is selected from the group consisting of peritoneal fluid, interstitial fluid, and transcellular fluid, and any combinations thereof.

* * * * *